United States Patent
Rung (10) Patent No.: US 9,179,230 B2
(45) Date of Patent: Nov. 3, 2015

(54) SYSTEM AND METHOD FOR MEASURING AND VALIDATING THE OCCLUSION EFFECT OF A HEARING AID USER

(75) Inventor: Martin Rung, Bronshoj (DK)

(73) Assignee: Widex A/S, Lynge (DK)

( * ) Notice: Subject to any disclaimer, the term of this patent is extended or adjusted under 35 U.S.C. 154(b) by 423 days.

(21) Appl. No.: 13/587,915

(22) Filed: Aug. 16, 2012

(65) Prior Publication Data

US 2012/0308020 A1 Dec. 6, 2012

Related U.S. Application Data (63) Continuation-in-part of application No. PCT/EP2010/059541, filed on Jul. 5, 2010.

(51) Int. Cl.
*H04R 25/00* (2006.01)
*A61B 5/12* (2006.01)

(52) U.S. Cl.
CPC *H04R 25/70* (2013.01); *A61B 5/12* (2013.01); *H04R 25/30* (2013.01); *H04R 2430/03* (2013.01); *H04R 2460/05* (2013.01)

(58) Field of Classification Search
CPC .... H04R 29/00; H04R 25/70; H04R 2400/01; H04R 2460/05; H04R 25/48; H04R 25/00; H04R 25/30; H04R 2430/03; A61B 5/12; G06F 17/50; G10L 21/0208
USPC ......... 381/110, 312, 316, 328, 58, 59, 60, 92, 381/23.1, 68, 71.14, 322; 700/94
See application file for complete search history.

(56) References Cited

U.S. PATENT DOCUMENTS

| 4,002,860 | A | * | 1/1977 | Terai et al. | 379/395 |
|---|---|---|---|---|---|
| 5,577,511 | A | | 11/1996 | Killion | |
| 2003/0012391 | A1 | * | 1/2003 | Armstrong et al. | 381/312 |
| 2003/0169891 | A1 | * | 9/2003 | Ryan et al. | 381/92 |
| 2009/0010456 | A1 | * | 1/2009 | Goldstein et al. | 381/110 |
| 2009/0129619 | A1 | * | 5/2009 | Nordahn | 381/328 |

FOREIGN PATENT DOCUMENTS

| WO | 2008017326 A1 | 2/2008 |
|---|---|---|
| WO | 2010083888 A1 | 7/2010 |

OTHER PUBLICATIONS

International Search Report with Written Opinion for PCT/EP2010/059541 dated Mar. 22, 2011.

* cited by examiner

*Primary Examiner* — Vivian Chin
*Assistant Examiner* — Ubachukwu Odunukwe
(74) *Attorney, Agent, or Firm* — Sughrue Mion, PLLC (57) ABSTRACT

A system for estimating the occlusion effect comprises a hearing aid adapted for being set up for operation in an occlusion measurement mode. The hearing aid comprises a first transducer (9) for transforming an acoustic sound level external to a hearing aid user's ear canal into a first electrical signal. The hearing aid comprises a second transducer (10) for transforming the acoustic sound level in the occluded ear canal into a second electrical signal. The system comprises a filter bank (21, 22) for splitting the first and the second digitized electrical signals into a first and a second band split digitized electrical signal, respectively and the estimated sound pressure must be a factor $\sqrt{r}$ larger than the estimated leakage when deciding if the estimated sound pressure in a given band can be applied in the calculation of the occlusion effect. The invention further provides a method for estimating the occlusion effect.

14 Claims, 4 Drawing Sheets

SYSTEM AND METHOD FOR MEASURING
AND VALIDATING THE OCCLUSION
EFFECT OF A HEARING AID USER

RELATED APPLICATIONS

The present application is a continuation-in-part of application PCT/EP2010/059541, filed on Jul. 5, 2010, in Europe and published as WO2012003855 A1.

BACKGROUND OF THE INVENTION

1. Field of the Invention

The present invention relates to estimation of occlusion in relation to hearing aid use. The invention more particularly relates to a system for estimating the occlusion effect comprising a hearing aid adapted for being set up for operation in an occlusion measurement mode.

When a hearing aid is placed in the ear of a user with an at least partially acoustically sealing ear mould it occludes the ear canal. Speech produced by the user generates not only sound pressure in the air but also vibrations in the wall of the ear canal. In the occluded ear this causes an elevation of the sound level of the user's own voice at the eardrum, especially in the lower frequencies. For many hearing aid users their own voice then sounds hollow or boomy, and this is known as the Occlusion Effect (OE). The OE can be perceived so annoying to the user, that it becomes a major obstacle in the hearing aid use.

When fitting a hearing aid it is in many cases convenient to be able to measure the OE in order to be able to reduce the OE as much as possible, considering that a sufficient amplification still has to be obtained. Possibilities for reducing OE are typically to increase the diameter of a ventilation channel in the ear plug or in the hearing aid.

The OE of a speaker's own voice is the ratio between the sound pressures generated at the eardrum by the voice when the ear canal is occluded by an ear mould and the hearing aid electrical amplification is switched off, and the sound pressures generated at the eardrum by the voice when the ear canal is open. I.e. $OE = p_{drum, occluded} / p_{drum, open}$.

Both of the quantities $p_{drum, occluded}$ and $p_{drum, open}$ are functions of time and frequency. So the OE is a time variant frequency dependent transfer function. To find the OE the two sound pressures ($p_{drum, occluded}$ and $p_{drum, open}$) must be determined with sufficient accuracy and resolution in both time and frequency. If $p_{drum, open}$ is zero the OE is not defined.

2. The Prior Art

In PCT/EP2009/050759, published as WO-A1-2010083888, it is explained how the OE can be found from a slightly different set of sound pressures ($p_{drum,occluded}$ and $p_{ext,occluded}$) and a correction term (that can be regarded constant for a given set-up). For the lower frequency range in which the OE is most significant, the estimation of the Occlusion Effect by $OE = k \cdot p_{drum, occluded} / p_{ext, occluded}$, (where k is a constant correction term) is relatively good. If $p_{ext,occluded}$ is zero the OE is not defined.

WO-A1-2008/017326 describes occlusion effect measurement by using the hearing aid, relying on the users own voice as a sound source.

To make a practical measurement of the OE, a measurement of the two sound pressures, $p_{drum, occluded}$ and $p_{ext, occluded}$, must be made. If the measurement of one or both sound pressures does not provide a sufficiently accurate result the OE value will not be valid and should be discarded. Different limitations in the procedure of the measurement of the sound pressures may in certain situations lead to inaccurate results. In order to discard those cases it is important to detect them properly.

As discussed in PCT/EP2009/050759 each of the two sound pressures can be captured by pressure sensitive transducers (such as a hearing aid microphone or a hearing aid receiver coupled to be used as a microphone). The output of the transducers can be analyzed in frequency bands by a filter bank (a bank of adjacent band pass filters), and the strength of the signal in each band be detected. The general assumption is that the signal strength in each band represents the sound pressure in that particular frequency band.

When measuring OE by using the hearing aid, the filter bank of the hearing aid, or an equivalent filter bank, is usually applied for splitting the obtained values of $p_{drum, occluded}$ and $p_{ext, occluded}$ into respective filter bands.

As also discussed in PCT/EP2009/050759 such frequency analysis can be compromised due to the finite, limited selectivity of the band pass filters. This is especially critical if the signal truly inside the frequency range of a band is low and the signal in a nearby band is higher. Due to the limited selectivity some of the higher signal power of the nearby band will be detected together with the low signal power inside the band. This means that a signal at one frequency which ideally should only be detected in one corresponding frequency band will also be detected in several neighboring frequency bands. This is here called leakage and may lead to erroneous results if measured values of the sound pressure severely contaminated with leakage are used for calculating the OE. The leakage may also be referred to as smearing or spectral splatter.

When the hearing aid users own voice is the sound source, the values of $p_{drum, occluded}$ and $p_{ext, occluded}$ are also expected to have broad and rather smooth frequency distributions on a long term basis (signal power spread across the entire speech spectrum). However, on a short term basis the power may be concentrated in narrow frequency bands (corresponding to the fundamental frequency and its harmonics during voiced speech). It is in this case not directly possible to see from the obtained values in the frequency bands which part of the signal is caused by an actual sound pressure level within the particular bands and which part is caused by leakage from other bands.

SUMMARY OF THE INVENTION

The invention, in a first aspect, provides a system for estimating the occlusion effect comprising a hearing aid adapted for being set up for operation in an occlusion measurement mode, said hearing aid comprising a first transducer adapted for transforming an acoustic sound level external to a hearing aid user's ear canal into a first electrical signal, and a second transducer adapted for when in said occlusion measurement mode, transforming the acoustic sound level in the occluded ear canal into a second electrical signal, said system further comprising analogue to digital converters for converting signals from said first and second transducer into digitized electrical signals, signal processing means comprising a filter bank adapted for when measuring the occlusion effect, splitting the first and the second digitized electrical signals into a first and a second frequency band split digitized electrical signal, respectively, sound pressure estimating means for estimating the sound pressure in each frequency band for both the first and the second frequency band split signal, leakage estimating means for estimating the leakage of signal into a frequency band from other frequency bands due to non ideal band pass filtering, wherein the system is adapted such that the estimated sound pressure must be larger than the estimated leakage when deciding if the estimated sound pressure in a given frequency band can be applied in the calculation of the occlusion effect.

Such a system will have the advantage of being able to assess if a measured sound pressure in a particular frequency band does represent input sound pressure centered at this band or is dominated by leakage. Further, the leakage estimating means will work from only evaluating the detected signal in each frequency band in the context of all the other bands. The detected signal in each frequency band is the only available information since the true spectrum of the sound pressure is unknown.

By discarding measurements of the occlusion effect where the leakage exceeds a given threshold, the accuracy of the overall measured occlusion effect can be considerably improved.

In an embodiment of a system for estimating the occlusion effect the estimated sound pressure must be at least a factor of $\sqrt{3}$ larger than the estimated leakage before the estimated sound pressure can be applied in the calculation of the occlusion effect. This has been found to give a reliable estimate of the occlusion effect.

In an embodiment of a system for estimating the occlusion effect the estimated sound pressure must be at least a factor of $\sqrt{3}$ larger than the estimated leakage before the estimated sound pressure can be applied in the calculation of the occlusion effect. This has been found to give a very accurate estimate of the occlusion effect.

In an embodiment of a system for estimating the occlusion effect the second transducer is a receiver of the hearing aid, where the receiver is being applied as a microphone when the hearing aid is in the occlusion measurement mode, and the receiver is being applied for providing amplified sound to a hearing aid user when the hearing aid is applied in a sound amplification mode. In a further embodiment the signal obtained by the receiver is equalized in order to be comparable with the signal obtained by said first transducer. One advantage of applying the receiver as microphone is, that less space will be taken up in the ear plug part of the hearing aid.

In a further embodiment of a system for estimating the occlusion effect the leakage estimating means includes the application of an analysis matrix, which provides an efficient way of estimating leakage of signal into one frequency band from neighboring or other frequency bands.

In a further embodiment of a system for estimating the occlusion effect data from frequency bands with estimated sound pressure below 60 dB SPL are discarded from the occlusion effect calculation.

In a further embodiment of a system for estimating the occlusion effect data all parts of the system are comprised in the hearing aid.

In a second aspect the invention provides a method for estimating the occlusion effect, said method applying a hearing aid set up for operation in an occlusion measurement mode, said method comprising the steps adapting in said hearing aid a first transducer for transforming an acoustic sound level external to a hearing aid users ear canal into a first electrical signal, and adapting in said hearing aid a second transducer for, when in said occlusion measurement mode, transforming the acoustic sound level in the occluded ear canal into a second electrical signal, converting analogue signals from said first and second transducer into digitized electrical signals, adapting signal processing means comprising a filter bank for, when measuring the occlusion effect, splitting the first and the second digitized electrical signals into a first and a second frequency band split digitized electrical signals, respectively, estimating the sound pressure in each frequency band for both the first and the second band split signal, estimating the leakage of signal into each frequency band from other frequency bands due to non ideal band pass filtering, and deciding if the estimated sound pressure in a given frequency band can be applied in the calculation of the occlusion effect, where this decision is based on measurements where the estimated sound pressure is larger than the estimated leakage.

BRIEF DESCRIPTION OF THE DRAWINGS

Embodiments of the invention will now be explained in further detail with reference to the figures.

DETAILED DESCRIPTION OF THE INVENTION

Figure 1:
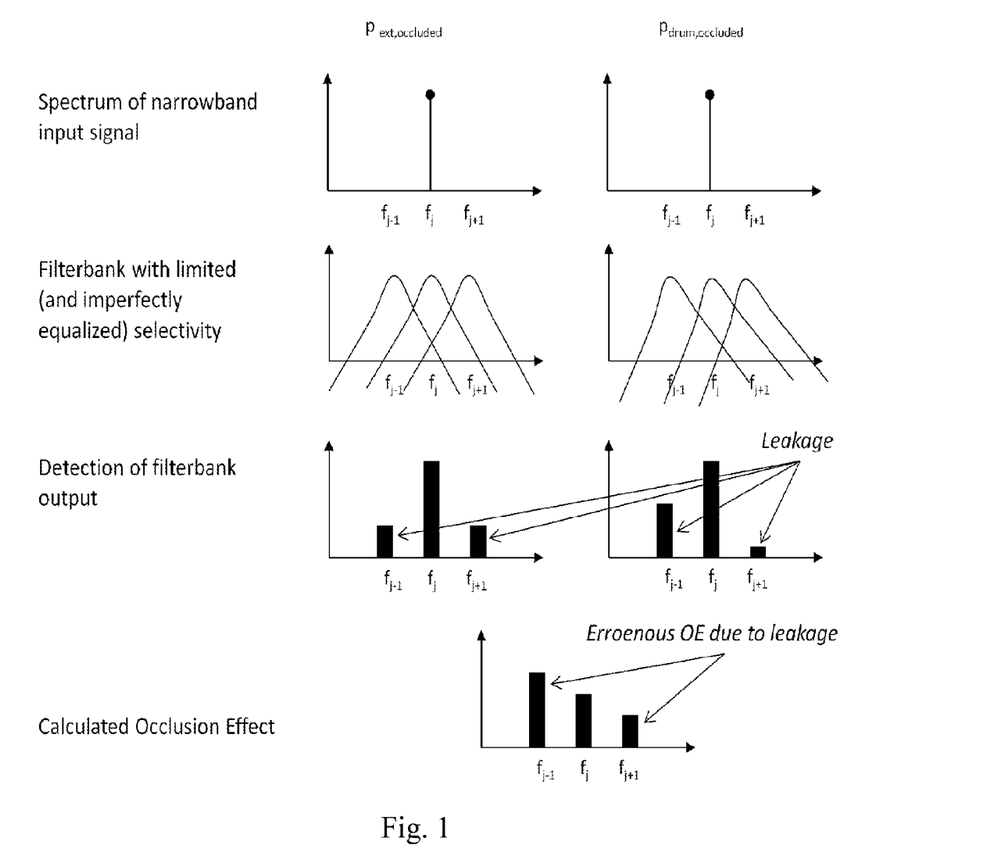
FIG. 1 illustrates in graphical form how the limited selectivity of the band pass filters of the filter bank can be the cause of leakage.

FIG. 1 show in graphical form a situation where the sound pressures, $p_{drum,\ occluded}$ and $p_{ext,\ occluded}$, consist of narrowband signals with power concentrated near $f_j$. At the frequencies $f_{j-1}$ and $f_{j+1}$ the power of both signals is zero. Consequently the OE is only defined at frequency $f_j$ and should not be calculated at other frequencies. All graphs in FIG. 1 show frequency along the horizontal axis and level or gain in dB along the vertical axis.

A band with band pass filter centered at $f_j$ detects the sound pressure well, as the signal power is centered in the pass band of the filter. The OE calculated from these values produce a valid OE value at frequency $f_j$. However due to the limited selectivity of the band pass filters the bands at $f_{j-1}$ and $f_{j+1}$ also detect a noticeable signal which we define as leakage.

As discussed in PCT/EP2009/050759 the amount of leakage in the measurements of the two sound pressures, $p_{drum,\ occluded}$ and $p_{ext,\ occluded}$, may differ if the transducers differ in frequency response and are not perfectly equalized. If the OE is calculated based on the measurements with severe leakage at $f_{j-1}$ and $f_{j+1}$, this may lead to OE values at these frequencies which are comparable to the OE value at frequency $f_j$ (or even larger)—although no OE values should actually have been calculated.

The example in FIG. 1 illustrates why it is essential to assess if a measured sound pressure in a particular frequency band does represent input sound pressure centered at this band or is dominated by leakage.

Figure 2:
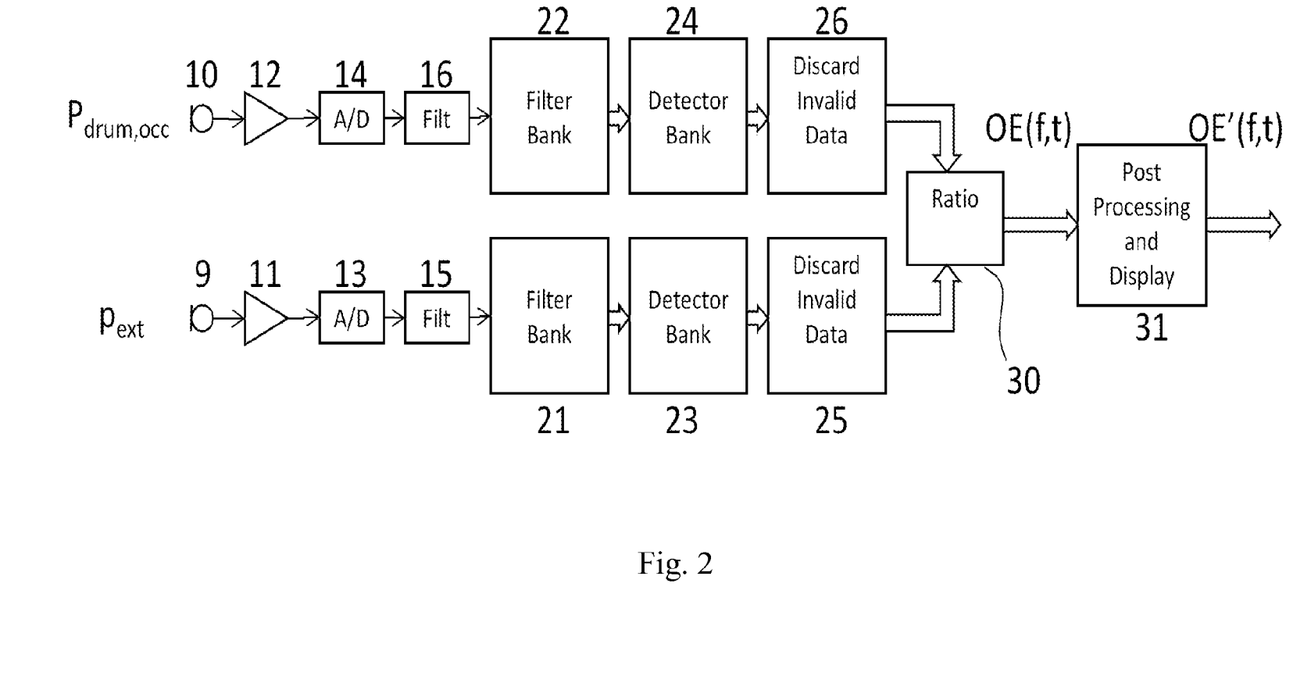
FIG. 2 illustrates an embodiment of a system for estimating the occlusion effect.

FIG. 2 shows an example of a system for measuring the occlusion effect. All or part of the system may be integrated in the hearing aid. Two sound pressure sensing transducers 9, 10 are shown, at least one being a microphone 9. The other may also be a microphone 10, but it could also be a receiver used as microphone. If the transducer 10 is a receiver it may be connected to the volume in front of the ear drum through a sound tube (not shown), or it may be arranged in the ear plug. The sound pressure external to the ear of the hearing aid user is denoted $p_{ext}$ and may be sensed by a usual microphone 9 of the hearing aid. When the hearing aid comprises two microphones, for the purpose of obtaining a specific directional sensitivity, any of the microphones may be applied for measuring the sound pressure external to the ear. In general, at least the two transducers 9, 10 are part of the hearing aid. The other components of the system for measuring the occlusion effect may be part of the hearing aid, but may also be arranged external to the hearing aid, e.g. as part of the computer used for fitting and programming the hearing aid.

The electrical signals from the two transducers 9, 10 are guided to pre-amplifiers 11, 12. The pre-amplifiers are ideally designed to have an idle noise floor somewhat lower than the idle noise floor of the transducer 9, 10 in order to not significantly add further noise to the microphone signal.

The pre-amplified signals are directed to analogue-to-digital (A/D) converters 13, 14 forming digitized electrical signals. Also the A/D converters should ideally have idle noise floor lower than the idle noise floor of the transducers 9, 10.

The two digitized electrical signals are preferably directed to filters 15, 16 applied for conditioning the signal in different ways. This could be band limiting the signal by e.g. high-pass filtering for removing low-frequency components below a frequency of interest. The filters could also be applied for correcting for an undesired frequency response of the sensing transducer. Such an undesired frequency response could originate from the acoustic coupling to the transducer or originate from the transducer element itself, such as the receiver when used as a microphone. Thus, an equalizing filter for correcting the frequency response of the receiver used as microphone (or if different types of microphones are applied) could be placed in the filter 16.

The filter 15 in the microphone branch for measuring the $p_{ext}$ may adjust the signal from representing the sound pressure at the microphone position to representing an estimate of the sound pressure in the open ear.

Spectral analyses of the signals are performed in the filter bank 21, 22, and the signal levels in each band can be observed in terms of sampling the level detectors, e.g. detecting root mean square (rms) values or other measures related to the level and other statistical properties of the signals. These values may be further processed in the hearing aid or may be exported to an external computer for further analysis, calculation of the ratio 30 (transfer function), correction and presentation.

One challenge in the approach to measuring ($p_{drum,\ occluded}/p_{ext,\ occluded}$) originates from using the hearing aid filter bank 21, 22 and the level detectors. A filter bank often comprises a number of band pass filters splitting the input signal into bands. The selectivity of hearing aid filter banks is not necessarily optimized for measurement purposes, but typically represents a balanced compromise with other properties of the filters. So these band pass filters will generally have a limited selectivity, and therefore lead to spectral leakage.

Calculating the transfer function for a band mostly containing spectral leakage from a narrow band signal located outside the pass band may lead to a wrong value for the band. So bands containing only (or mainly) leakage must be identified and discarded 25, 26.

The two signals used to calculate the transfer function are captured by two different transducers. If these two transducers do not have similar frequency responses the effects of spectral leakage becomes much more critical. This may be solved by applying an equalization filter in order to give both transducers the same frequency response.

The Occlusion Effect for data found to be valid is calculated in the ratio block 30. Post processing of the data may be performed in the post processing and display block 31. Post processing may be applied to reduce the amount of data or emphasize certain aspects of the data for a suitable display or other means of communication—eventually other decision making or advising processes. Post processing may include time and frequency weighting and averaging. Finally, the data are displayed in a suitable form. The display would typically be on a monitor external to the hearing aid.

The following description concentrates on a method to assess detected output values of a filter bank to estimate the amount of leakage in each value. Based on that estimated leakage the value may either be accepted (if leakage can be neglected or corrected for) or discarded (if leakage cannot be neglected or corrected for). If the measurement of both or just one of the two sound pressures in a particular band is discarded due to leakage, the calculation of an erroneous OE value can be avoided.

In PCT/EP2009/050759 an expression for the signal power observed in the j'th band of the filter bank is expressed this way:

$$X_j = \sum_{k=1}^{N} F_{j,k}^2 E_k^2 T_k^2 (Ps_k + Pn_k)$$

where $F_{j,k}$ is the frequency response in band j to a signal in band k. $E_k$ is the frequency response in band k of the equalization filter. $T_k$ is the sensitivity to sound pressure in band k. $Ps_k$ is the power of the sound pressure signal in band k. $Pn_k$ is the power of noise in band k.

Neglecting the noise as this description concentrates on the leakage we get:

$$X_j = \sum_{k=1}^{N} F_{j,k}^2 E_k^2 T_k^2 (Ps_k)$$

This can be expanded into:

$$X_j = F_{j,j}^2 E_j^2 T_j^2 Ps_j + \sum_{k=1}^{(j-1)} F_{j,k}^2 E_k^2 T_k^2 Ps_k + \sum_{k=(j+1)}^{N} F_{j,k}^2 E_k^2 T_k^2 Ps_k$$

and so $$X_j = Y_j + L_j$$

where $$Y_j = F_{j,j}^2 E_j^2 T_j^2 Ps_j$$

$$L_j = \sum_{k=1}^{(j-1)} F_{j,k}^2 E_k^2 T_k^2 Ps_k + \sum_{k=(j+1)}^{N} F_{j,k}^2 E_k^2 T_k^2 Ps_k$$

$Y_j$ is the contribution to $X_j$ that is not caused by leakage and so is the desired measured value.

Formulated this way a measured $X_j$ should be accepted as a valid measurement only if the leakage is so small that it can be neglected. For practical use it can be determined by setting a threshold requiring that $L_j$ is less than a certain fraction of $X_j$:

$$L_j < X_j/r \Leftrightarrow (X_j/L_j) > r \Leftrightarrow X_j > rL_j$$

r is chosen according to a compromise between how much leakage can be accepted in a measured value and how many values will be discarded due to leakage. Preferably, the estimated sound pressure is a factor of 2 larger than the leakage, and more preferably it is a factor of 3 larger.

Because the only information available for this assessment of $X_j$ is the set of measurements in all bands $[X_1, X_2, \ldots X_j, X_N]$, $L_j$ has to be calculated from this set of values.

If both $X_j$ and $L_j$ are known then $Y_j$ can be found by:

$$Y_j = X_j - L_j$$

So in principle an ideal measurement free of leakage can be calculated. However, if the calculation of $L_j$ is not very accurate then $L_j$ has to be sufficiently small compared to $X_j$ in order to lead to a useful $Y_j$. This leads again to the requirement that $L_j$ is less than a certain fraction of $X_j$, if $Y_j$ shall be used.

The following describes how to estimate from an evaluation of just the set of measurements in all bands $[X_1, X_2, \ldots X_j, \ldots X_N]$.

For a convenient description of the method of estimating the leakage a formulation in terms of vectors and matrices is used.

The above equations can easily be reformulated as follows:
Let P be the N element column vector where element j equals $Ps_j$.
Let X be the N element column vector where element j equals $X_j$.
Let Y be the N element column vector where element j equals $Y_j$.
Let L be the N element column vector where element j equals $L_j$.
Let T be an N by N diagonal matrix where element j,j equals $T_j^2$.
Let E be an N by N diagonal matrix where element j,j equals $E_j^2$.
Let F be an N by N matrix where element j,k equals $F_{j,k}^2$.

So the above expression of the detected value in the j'th band $$X_j = \sum_{k=1}^{N} F_{j,k}^2 E_k^2 T_k^2 (Ps_k)$$

can be re-formulated to $$X = FETP$$

As has been explained above X contains leakage. Multiplying the input vector P by a diagonal matrix does not introduce leakage. So the multiplication by the matrices T and E does not cause leakage because both are diagonal matrices.

The leakage is caused by the multiplication by F (i.e. the analysis in the filter bank) which is a matrix containing non zero elements outside the diagonal. If the filters of the filter bank were ideal bandpass filters the matrix describing it would be a diagonal matrix. In order to separate the non-leakage part and the leakage part of the detected values F can be split into an ideal filter bank D and the remaining part of F. D is a diagonal matrix equal to the diagonal of F.

Introducing $$D = \text{diagonal}(F)$$

we get $$X = FETP \Leftrightarrow$$

$$X = (D + F - D)ETP \Leftrightarrow$$

$$X = DETP + (F - D)ETP$$

This corresponds to $$X = Y + L$$

where the non leakage component of X is $$Y = DETP$$

and the leakage component of X is $$L = (F - D)ETP$$

Y is the detected values if the filter bank were an ideal filter bank. It is the input vector multiplied only by diagonal matrices and so no leakage is created. It is the non-leakage component of X.

Correspondingly L includes a multiplication by (F−D) which is a matrix with an all zero diagonal. So L contains no non-leakage component and is thus the pure leakage component of X.

From the expression of X we get $$X = FETP \Leftrightarrow$$

$$F^{-1}X = F^{-1}FETP \Leftrightarrow$$

$$F^{-1}X = ETP$$

Using this in the expression of L we get $$L = (F - D)F^{-1}X$$

or $$L = MX \text{ where } M = (F - D)F^{-1}$$

By this we have now achieved an expression for the leakage, L, from only the detected values, X. The leakage, L, is calculated from the detected values, X, by multiplication by the analysis matrix, M.

If L is known, Y can be found as well:

$$X = Y + L \Leftrightarrow$$

$$Y = X - L$$

In order to get a measurement of P a calibration C has to be found so that:

$$CY = P \Leftrightarrow$$

$$CDETP = P \Leftrightarrow$$

$$CDET = I \Leftrightarrow$$

$$C = (DET)^{-1} \Leftrightarrow$$

$$C = T^{-1}E^{-1}D^{-1}$$

where I is the identity matrix in which the elements on the main diagonal are equal to 1 and all other elements are equal to 0. The simplest approach to identify the valid measurements is exploiting that if the leakage $L_j$ is so small that it can be neglected, then $X_j$ may be used instead of $Y_j$:

Calculate L from X.
If $X_j > r$ then accept $X_j$, else discard $X_j$.
If $X_j$ accepted then use $C_j X_j$ as valid measurement of $P_j$ and $p_j = \text{sqrt}(P_j)$ An alternative approach to identify the valid measurements of $P_j$ (and so $p_j$) is:

Calculate L from X.
Calculate Y from X and L.
If $Y_j > (r-1) L_j$ then accept $Y_j$, else discard $Y_j$
If $Y_j$ accepted then use $C_j Y_j$ as valid measurement of $P_j$ and $p_j = \text{sqrt}(P_j)$ An illustrative example demonstrating the principles is given in the following.

A simple system analyzing the signal in only four frequency bands is chosen for this example, but the principles are applicable for other numbers of bands as well.

These four bands could for example be the four lowest bands of a hearing aid filter bank, where the four bands cover the frequency range in which the occlusion effect is to be measured. The total number of bands could for example be 15.

In this example the approach where elements in CX are used as the estimate for the elements in P if the influence of leakage is found to be sufficiently low.

The power transfer function matrices of the system (as described above) are:

$$T = \begin{pmatrix} 0.28 & 0 & 0 & 0 \\ 0 & 0.50 & 0 & 0 \\ 0 & 0 & 1.70 & 0 \\ 0 & 0 & 0 & 0.80 \end{pmatrix}$$

$$E = \begin{pmatrix} 1.90 & 0 & 0 & 0 \\ 0 & 1.10 & 0 & 0 \\ 0 & 0 & 0.50 & 0 \\ 0 & 0 & 0 & 1.40 \end{pmatrix}$$

$$F = \begin{pmatrix} 1 & 0.10 & 0.03 & 0.01 \\ 0.10 & 1 & 0.10 & 0.03 \\ 0.03 & 0.10 & 1 & 0.10 \\ 0.01 & 0.03 & 0.10 & 1 \end{pmatrix}$$

$$C = \begin{pmatrix} 1.88 & 0 & 0 & 0 \\ 0 & 1.82 & 0 & 0 \\ 0 & 0 & 1.18 & 0 \\ 0 & 0 & 0 & 0.89 \end{pmatrix}$$

Note that T, E and C (the sensitivity, equalization and calibration, respectively) are all diagonal matrices while F (frequency response)—although having the largest values in the diagonal—has non-zero elements outside the diagonal.

Figure 3:
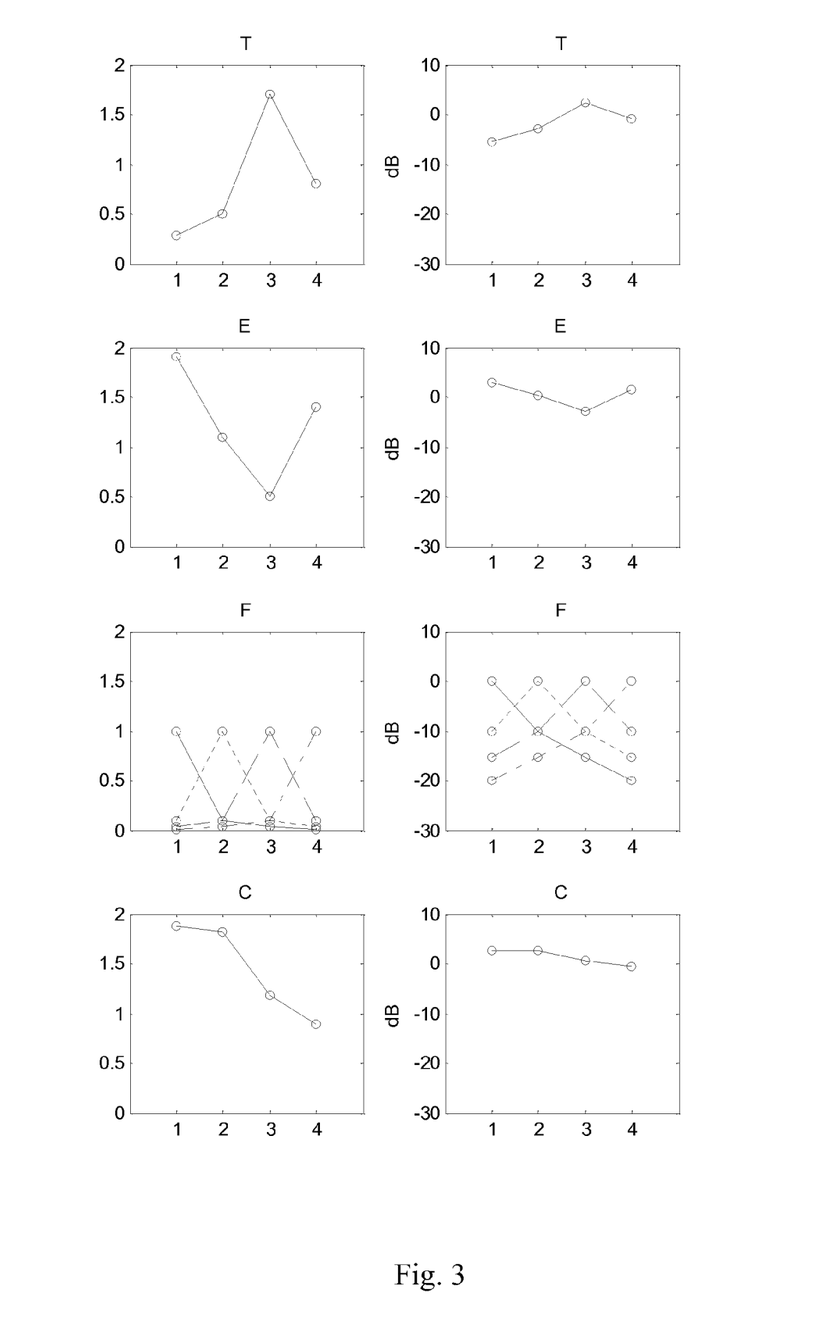
FIG. 3 illustrates graphs of power transfer functions in a simple example calculating the leakage in only four frequency bands.

FIG. 3 shows graphs of these transfer functions. For T, E and C the elements of the diagonal are shown as a connected curve. For F the elements of each row are shown as connected curves. The graphs in the left column show the matrix elements on a linear y axis, while the graphs in the right column show matrix elements on a y axis in dB.

The vector representing the power of the input signal, P, is:

$$P = \begin{pmatrix} 1 \\ 0.01 \\ 0.5 \\ 0.01 \end{pmatrix}$$

Such a signal could occur in the case where the fundamental frequency of some voiced speech is located in the first band and second harmonic frequency is located in the third band. Only little signal power is located in the second and fourth band.

The resulting signal power vectors X, L and CX then become:

$$X = \begin{pmatrix} 0.545 \\ 0.102 \\ 0.443 \\ 0.059 \end{pmatrix}$$

$$L = \begin{pmatrix} 0.013 \\ 0.096 \\ 0.018 \\ 0.048 \end{pmatrix}$$

$$CX = \begin{pmatrix} 1.025 \\ 0.185 \\ 0.521 \\ 0.052 \end{pmatrix}$$

Figure 4:
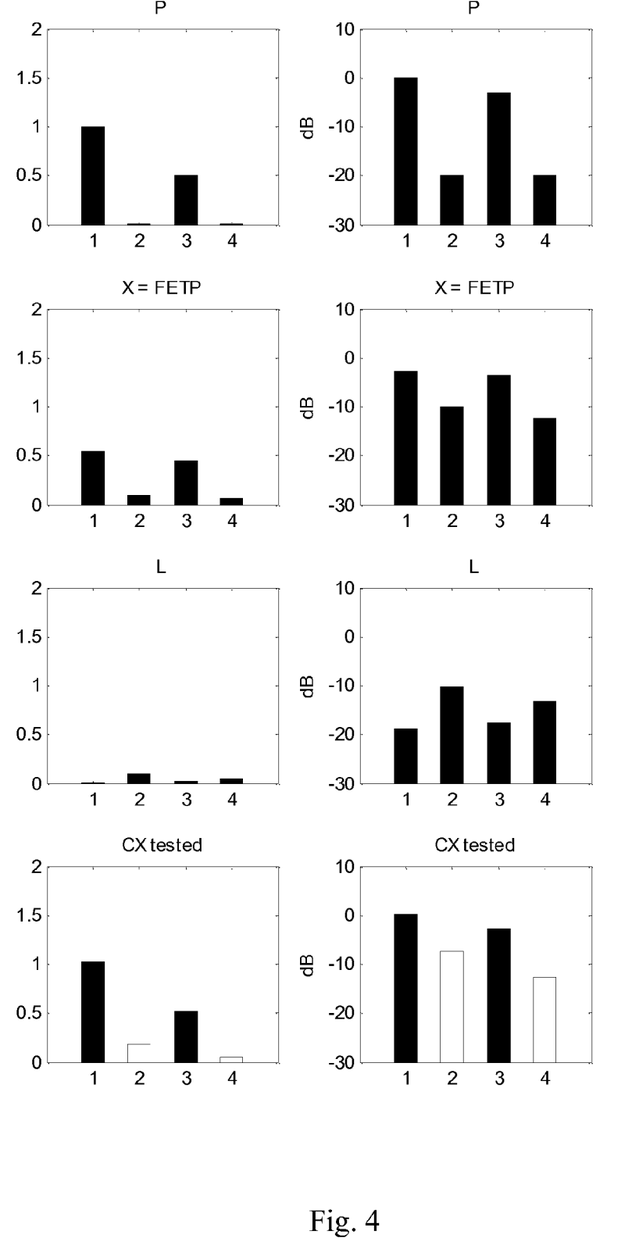
FIG. 4 illustrates graphs of resulting power vectors for the example in FIG. 3.

FIG. 4 shows P, X, L and CX. The graphs in the left column show the vector elements on a linear y axis, while the graphs in the right column show vector elements on a y axis in dB.

An element of CX is shown in white if the element of X has been tested and discarded by the comparison with corresponding element of r L. r equal to 2 has been used in this example.

It can be seen that the values for the first and third band have been accepted, while the values for the second and fourth band were discarded.

Comparing the estimated input, CX, with the true input, P, it can be seen that the discarding process has served its purpose: The accurate estimates have been correctly accepted and the inaccurate estimates have been correctly discarded.

In the accepted first and third band CX approximates P well within a fraction of a dB. In the discarded second and fourth band CX deviates substantially from P with several dB.

The invention claimed is:

1. A system for estimating the occlusion effect, said system comprising:
   a hearing aid capable of being set up for operation in an occlusion measurement mode, said hearing aid comprising
   a first transducer configured to transform an acoustic sound level external to a hearing aid user's ear canal into a first electrical signal, and
   a second transducer configured to, when in said occlusion measurement mode, transform the acoustic sound level in the occluded ear canal into a second electrical signal, said system further comprising
   analogue to digital converters for converting signals from said first and second transducer into digitized electrical signals,
   a signal processor comprising a filter bank configured to, when measuring an occlusion effect, split the first and the second digitized electrical signals into a first and a second frequency band split digitized electrical signal, respectively,
   a sound pressure estimator for estimating the sound pressure in each frequency band for both the first and the second frequency band split signal, and
   a leakage estimator for estimating the leakage of signal into a frequency band from other frequency bands due to non ideal band pass filtering,
   wherein the system is configured such that the estimated sound pressure must be larger than the estimated leakage when deciding if the estimated sound pressure in a given frequency band can be used in the calculation of the occlusion effect.

2. The system according to claim 1, wherein the estimated sound pressure in a frequency band must be at least a factor of $\sqrt{2}$ (square root of two) larger than the estimated leakage of sound pressure into the frequency band as a condition for applying the estimated sound pressure in the calculation of the occlusion effect.

3. The system according to claim 1, wherein the estimated sound pressure in a frequency band must be at least a factor of $\sqrt{3}$ (square root of three) larger than the estimated leakage of sound pressure into the frequency band as a condition for applying the estimated sound pressure in the calculation of the occlusion effect.

4. The system according to claim 1, wherein said second transducer is a receiver of the hearing aid, said receiver being applied as a microphone when the hearing aid is in the occlusion measurement mode, and said receiver providing amplified sound to a hearing aid user when said hearing aid is operated in a sound amplification mode.

5. The system according to claim 4, wherein the signal obtained by the receiver is equalized in order to be comparable with the signal obtained by said first transducer.

6. The system according to claim 1, wherein said leakage estimator includes the application of an analysis matrix.

7. The system according to claim 1, wherein data from frequency bands with estimated sound pressure below 60 dB SPL are discarded from the occlusion effect calculation.

8. The system according to claim 1, wherein all parts of the system are comprised in the hearing aid.

9. A method for estimating the occlusion effect, said method using a hearing aid set up for operation in an occlusion measurement mode, said method comprising the steps configuring a first transducer in said hearing aid for transforming an acoustic sound level external to a hearing aid users ear canal into a first electrical signal, configuring a second transducer in said hearing aid for, when in said occlusion measurement mode, transforming the acoustic sound level in the occluded ear canal into a second electrical signal, converting analogue signals from said first and second transducer into digitized electrical signals, configuring a signal processor comprising a filter bank for, when measuring the occlusion effect, splitting the first and the second digitized electrical signals into a first and a second frequency band split digitized electrical signals, respectively, estimating a sound pressure in each frequency band for both the first and the second band split signal, estimating a leakage of signal into each frequency band from other frequency bands due to non ideal band pass filtering, and deciding if the estimated sound pressure in a given frequency band can be used in the calculation of the occlusion effect, where this decision is based on measurements where the estimated sound pressure is larger than the estimated leakage.

10. A method according to claim 9, wherein the decision is based on measurements where the estimated sound pressure is larger than the estimated leakage by a factor of at least $\sqrt{2}$.

11. A method according to claim 10, wherein the factor is selected to a value of at least $\sqrt{3}$.

12. The method according to claim 9, wherein the configuring of a second transducer includes selecting the receiver of the hearing aid as the second transducer, said receiver being used as a microphone when the hearing aid is in the occlusion measurement mode, and said receiver being used for providing amplified sound to a hearing aid user when said hearing aid is used in a sound amplification mode.

13. The method according to claim 12, further equalizing the signal obtained by the receiver in order to make this signal comparable with the signal obtained by said first transducer.

14. The method according to claim 9, comprising discarding data from frequency bands with estimated sound pressure below 60 dB SPL, from the occlusion effect calculation.

* * * * *